United States Patent [19]

Goodsir et al.

[11] Patent Number: 4,753,345
[45] Date of Patent: Jun. 28, 1988

[54] HYPODERMIC SYRINGE TRAY

[75] Inventors: Stephen W. Goodsir, Wayne, Pa.; Dominic A. Ventura, Berlin, N.J.

[73] Assignee: American Home Products Corporation, New York, N.Y.

[21] Appl. No.: 620,604

[22] Filed: Jun. 14, 1984

[51] Int. Cl.⁴ .............................................. B65D 17/16
[52] U.S. Cl. ...................................... 206/366; 206/365
[58] Field of Search ................................ 206/365, 366

[56] References Cited

U.S. PATENT DOCUMENTS

| | | | |
|---|---|---|---|
| 2,084,540 | 6/1937 | Smith | 206/365 |
| 2,955,705 | 10/1960 | Krueger, Sr. et al. | 206/365 |
| 3,032,186 | 5/1962 | Jenkins | 206/365 |
| 3,133,635 | 5/1964 | Gordon et al. | 206/366 |
| 3,207,302 | 9/1965 | Hobbs | 206/366 |
| 3,439,796 | 4/1969 | Zykoski | 206/366 |
| 3,489,268 | 1/1970 | Meierhoefer | |
| 3,494,458 | 2/1970 | Meierhoefer | |
| 3,727,749 | 4/1973 | Martin | 206/366 |
| 3,783,997 | 1/1974 | Brown | 206/365 |
| 4,113,090 | 9/1978 | Carstens | 206/365 |

Primary Examiner—Joseph Man-Fu Moy
Attorney, Agent, or Firm—Richard K. Jackson

[57] ABSTRACT

A hypodermic syringe tray adapted to hold at least one hypodermic syringe, comprising a barrel, plunger, cannula and cannula cover, in such manner as to secure said cannula cover and said plunger during thermal sterilization of the syringe and its contents.

10 Claims, 1 Drawing Sheet

HYPODERMIC SYRINGE TRAY

BACKGROUND OF THE INVENTION

Conventionally, sterile parenteral dosage forms of solutions or dispersions of biologically compatible liquids with or without medicament for intravenous, intramuscular, subcutaneous or similar routes of administration are placed in sterile injectable form by withdrawing sterile material from a bottle with a sterile hypodermic syringe and needle just prior to administration or, in the case of disposable hypodermic syringes, a presterilized parenteral solution or dispersion is prepared and filled into the sterile syringe barrel for subsequent use with a syringe holder dispensing device. Although aspectic manufacturing of prefilled disposable syringes is possible, it does not offer the same confidence as terminal sterilization.

Terminal sterilization of parenteral solutions and disposable syringes would be accomplished after filling the syringe, as the final production step. However, attempts to sterilize parenteral solutions contained within a disposable syringe employing conventional sterilization techniques results in loss of solution by expulsion of the plunger, displacement of the cannula cover and/or distortion of the secondary packaging container as a consequence of internal pressure created by liquid and gas (headspace) expansion.

DESCRIPTION OF THE INVENTION

In accordance with this invention there is provided a hypodermic syringe tray, adapted to hold at least one hypodermic syringe, comprising a barrel, plunger, cannula and cannula cover, in such manner as to secure said cannula cover and said plunger during thermal sterilization of the syringe and its contents.

The hypodermic syringe tray of this invention represents bottom, side walls and end walls which, when fitted with a lid or inserted into a bottom shell of a lidded container, constitutes a package for distribution and/or storage of disposable syringes. Any conventional packaging mechanics which provide tamper proofing, labeling, viewing or assembling characteristics not inconsistent with the requirements of the tray of this invention may be incorporated into the hypodermic syringe package without departing from the gist of this invention The end wall of the hypodermic syringe tray against which the open (proximal) end of the barrel of the syringe abuts, may optionally be filled with cylindrical fingers which are of smaller diameter than the interior dimension of the syringe barrel so that they project into the proximal end of the syringe barrel and contact the plunger bushing (threaded stud).

Between the side walls of the hypodermic syringe tray of this invention, and either integral therewith or attached thereto, there is disposed at least one conventional septal cradle adapted to receive and support the barrel of the syringe. In addition, disposed between the tray's sidewalls is a septal locking cradle adapted to secure the syringe cannula cover and abut the distal end of the syringe ferrule, said locking cradle being situated at a distance from the tray end wall closest to the open (proximal) end of the syringe barrel so that longitudinal movement of a syringe resting on said septal cradle and septal locking cradle is opposed by said septal locking cradle and end wall. Thus, the septal locking cradle serves three purposes; it supports the hypodermic syringe above the tray bottom, locks the cannula cover to the distal end of the ferrule and abuts the distal end of the ferrule, thereby preventing loosening of the cannula cover and expulsion of the plunger during thermal sterilization of the syringe and its liquid contents.

The cannula cover conventionally employed with disposable syringes is made of rubber. It is apparent, however, that any deformable material which will withstand the rigors of thermal sterilization while maintaining its integrity as a needle cover may be used. Applicants prefer rubber as a cannula cover when used in the syringe tray of this invention because rubber, and especially natural or chlorobutyl rubber, readily deforms when inserted into the septal holding cradle, remain securely held in the septal holding cradle during thermal sterilization of the tray and syringes, retain their integrity as covers during subsequent storage and recover their original shape when withdrawn from the septal holding cradle for ease of removal (no adherence to the needle) just prior to administration of the contents of the syringe.

By thermal sterilization applicant means to embrace conventional high temperature sterilization techniques employed to produce aseptic medicinal formulations and equipment, such as steam sterilization which involves exposure to steam in an autoclave for periods of from about 15 minutes to about one hour at autogenous pressure and temperatures ranging from about 110° C. to about 125° C. Dry heat may also be employed to sterilize equipment and medicinal formulations, in which case temperatures in the range of about 130° C. to about 150° C. for periods of from about 1 to 3 hours are applicable.

The ferrule attaching the cannula to the syringe barrel is made of metal, such as aluminum, which is crimp connected to the glass barrel, or nylon which is molded to convert the barrel and cannula.

The septal holding cradle may present any of several cradle conformations adapted to securely hold the cannula cover in place. For example, a simple vee block construction is applicable whereby the septum is in essence countersunk in such manner as to breach its upper side thereby providing a surface suitable to crimp the cannula cover and hole it in position. Alternatively, a keyway opening in the septal cradle provides a more complex holding system whereby the syringe and cannula cover are forced down the keyway to provide a holding lock.

The hypodermic syringe tray of this invention may be molded as a unitary work piece or produced as components for ultimate assembly by techniques well known to the art. The hypodermic syringe trays of this invention are made of any material which will undergo high temperature sterilization conditions without deforming. Aluminum is an excellent metal for tray production. Plastic materials capable of withstanding thermal sterilization conditions, such as polystyrene and polycarbonates, as well as copolymers of these resins, are similarly applicable.

The accompanying drawings illustrate embodiments of this invention:

Figure 1:
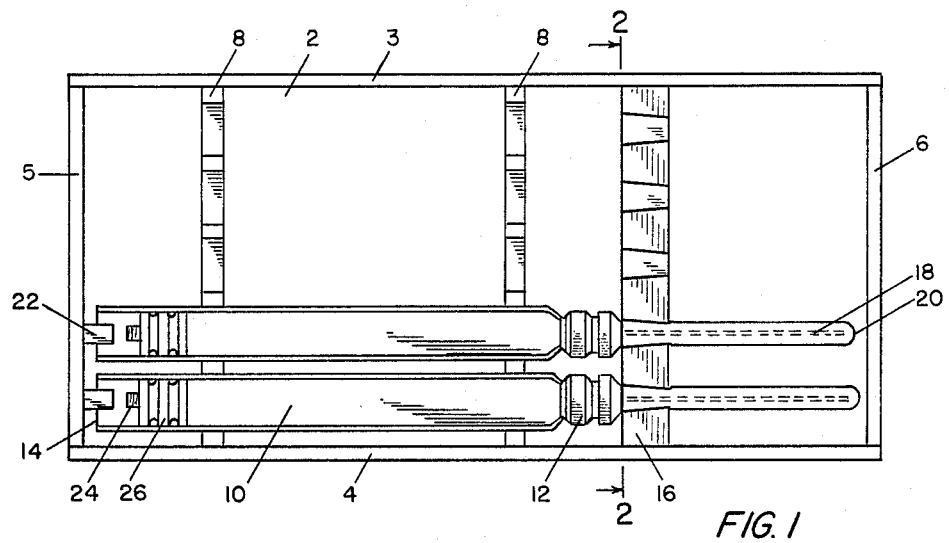
FIG. 1 is a plan view of the hypodermic syringe tray containing two syringes.
Figure 4:
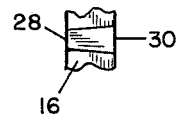
FIG. 4 is a top view of the cannula retaining cradle depicting the vee block configuration reversed from that shown in FIG. 1.

In FIG. 1 there is depicted a hypodermic syringe tray comprising a bottom 2, two side walls 3 and 4, and two end walls 5 and 6. Disposed within said tray are septal cradles 8 which may be situated anywhere within the tray to support the glass barrel 10 of a syringe at some point between the ferrule 12 and proximal end of the barrel 14. In actual practice a single septal cradle 8 is sufficient to support the barrel of the syringe. Also disposed within said tray is a septal holding cradle 16 which is situated to receive the cannula 18 and cannula cover 20 of a syringe. FIG. 1 also depicts the optional presence of a cylindrical finger 22 which extends from end wall 5 into the proximal end of the syringe barrel 10 to about the plunger bushing 24 which is attached in the plunger 26. The configuration of the septal holding cradle design of the cannula retainer may best be seen in the absence of a depicted syringe as shown in top view FIG. 4, to consist of a slot in septal holding cradle 16, constructed such that the opening at 28 is smaller than that at 30, thereby pinching the rubber cannula cover at 28. This vee block type of cannula retainer may be disposed so that the narrow portion of the opening 28 is placed near ferrule 12 or away from ferrule 12.

Figure 2:
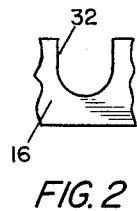
FIG. 2 is a cross section of the tray depicted in FIG. 1, taken on line 2—2, to show the configuration of the cannula retaining cradle as a straight wall rather than a vee block depicted in FIG. 1.
Figure 3:
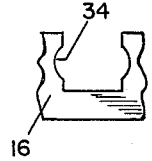
FIG. 3 is a cross section of the tray depicted in FIG. 1, taken along 2—2, to show a different configuration of the cannular retaining cradle as a straight wall, such as is shown in FIG. 2, provided with a curvilinear portion in which the cannula may be seated.

FIGS. 2 and 3 represent variations about the septal holding cradle-cannula retainer 16 such that a straight wall as depicted in FIG. 2 serves to depress the rubber cannula cover to a constant degree throughout the length of contact, and a straight wall 32 with curvilinear portion 34 to seat the cannula cover as depicted in FIG. 3, designed to require greater force in loading and unloading a syringe from the tray while maintaining constant pressure on the cannula cover when seated between the cusps of the cradle wall.

What is claimed is:

1. In a package bottom tray comprising a bottom, side walls and end walls, constructed to house at least one sterile, disposable hypodermic syringe equipped with a deformable cannula cover and containing a sterile liquid, the improvement which comprises cannula cover- and plunger-securing means disposed in such manner as to minimally exert an equal and opposite force to that exerted against said cannula cover and plunger by thermal expansion of liquid contained within said syringe, said cannula cover securing means abutting the distal end of the syringe ferrule, locking said cannula cover thereo.

2. A package bottom tray as described in claim 1 in which said sterile liquid contains a medicament.

3. A package bottom tray as described in claim 1 in which said cannula cover-securing means is a vee block disposed in such manner in relationship to said cannula cover to exert a frictional force in an opposite direction to that of liquid expansion within said syringe.

4. A package bottom tray as described in claim 1 in which said plunger-securing means is the end wall of said package bottom tray.

5. A package bottom tray as described in claim 1 in which said plunger-securing means is a finger integral with said end wall, projecting substantially perpendicular from said end wall to contact the plunger bushing.

6. A plunger-securing means as described in claim 5 in which said finger is cylindrical.

7. A plunger-securing means as described in claim 5 in which said finger is a truncated conical projection.

8. A package bottom tray as described in claim 1 in which there is at least one septal cradle to support said syringe barrel.

9. A package bottom tray - hypodermic syringe assembly comprising the package bottom tray of claim 1, having disposed therein at least one hypodermic syringe comprising a cartridge and hypodermic needle joined by a ferrule, said needle being disposed in a cannula cover, said cartridge and needle housing a sterile liquid contained by a plunger disposed within said cartridge and a core pin disposed to seal the open end of said needle, said cartridge resting on a septal cradle disposed in the bottom tray with said cannula cover being held by cannula cover-securing means which prevent longitudinal displacement of the cover while permitting vertical removal of the entire syringe, said cannula cover-securing means abutting said ferrule and preventing movement of the open end of said cartridge from said tray end wall.

10. A package bottom tray - hypodermic syringe assembly as described in claim 9 in which said sterile liquid contains a medicament.

* * * * *